United States Patent
Chen et al.

(10) Patent No.: US 6,936,463 B1
(45) Date of Patent: Aug. 30, 2005

(54) METHOD AND DEVICE FOR MAKING DIFFERENT THICKNESS OF BIOFILMS

(76) Inventors: Chin-Yu Chen, 2F, No.21, Ln.295, Ching-Shin St., ChungHo City, Taipei Hsien (TW); Woan-Jiun Swei, 2F, No.21, Ln.295, Chin-Shin St., ChungHo City, Taipei Hsien (TW)

( * ) Notice: Subject to any disclaimer, the term of this patent is extended or adjusted under 35 U.S.C. 154(b) by 0 days.

(21) Appl. No.: 10/820,802

(22) Filed: Apr. 9, 2004

(51) Int. Cl.⁷ .............................................. C12M 1/00
(52) U.S. Cl. ............................. 435/307.1; 435/309.2; 435/309.4
(58) Field of Search ........................ 435/307.1, 308.1, 435/309.2, 309.4

(56) References Cited

U.S. PATENT DOCUMENTS 5,605,836 A * 2/1997 Chen et al. .............. 435/305.4
6,767,734 B2 * 7/2004 Liu .......................... 435/293.1

* cited by examiner

*Primary Examiner*—David Redding
(74) *Attorney, Agent, or Firm*—Troxell Law Office, PLLC

(57) ABSTRACT

A method and device for making different thickness of biofilms is disclosed. It comprises: (a) a pair of pentagonal dish including a dish bottom and a dish cover; (b) an internal thickness module having a number of protrusions of different heights or of the same height The method and device also offers a simple way for testing the effect of various biofilms on the adhesion and corrosion of different materials.

4 Claims, 8 Drawing Sheets

METHOD AND DEVICE FOR MAKING DIFFERENT THICKNESS OF BIOFILMS

FIELD OF THE INVENTION

This invention relates to method and device for making different thickness of biofilms and for determining the effect of various biofilms on the adhesion and corrosion of different materials.

BACKGROUND OF THE INVENTION

The present invention is an improvement on the making biofilms systems disclosed in our patent U.S. Pat. No. 5,605,836 for MODULAR METHOD AND DEVICE FOR THE EVALUATION OF THE BIOCIDE TO PENETRATE BIOFILM incorporated herein by reference.

Biofilms caused by various kinds microbiological contamination occur frequently in the conveying system of food processing plants, implantable and insertable medical devices, airplane fuel tanks and pipeline filters, waste water discharge lines of nuclear power plant heat exchangers, pulp and paper industrial processes and so on. Such biofilms not only cause the affected pipelines to narrow, reducing their capacity and wasting energy but also could contribute to corrosion of the pipelines and endanger the entire system. In food and pulp processing plants, biofilms in conveying systems could additionally cause serious quality control problems. In hospitals, contaminated equipments and devices could infect patients. In aviation, once biofilms are developed in fuel lines, they could cause deterioration in the quality of the fuel and/or seriously affect air safety by damaging the integrity of the fuel lines by pitting the wall surface of the fuel lines so covered. Needless to say, how to overcome the problems caused by biofilns is a very important and pressing problem.

The effectiveness of these various biocides is expressed in terms of MIC—minimal inhibitory concentration. However, MIC is measured against microbiological concentrations in planktonic state only, and is quite irrelevant against microbes that have become sessile. It is not unusual to use biocides in concentrations of several hundred times, even thousand times the MIC to deal with sessile microbiological contamination. The main reason for this is that once biofilms are developed, they tend to act as barriers against the biocide. Indeed, many research results have already indicated that the use of MIC values to indicate biocide effectiveness is misleading, because the MIC values can't represent the actual effect of biocides on microorganisms that have developed biofilm.

In order to truly evaluate the effectiveness of a biocide against both planktonic and sessile microbes, a way must be developed to create biofilms of different thickness in the laboratory. At the present time, many different systems of biofilm reactors are being tested. For example, U.S. Pat. No. 6,361,963 to Smith et al. discloses a method and apparatus for determining the effect of various agents on the growth of biological material, microbially-influenced corrosion and the deposition of organic and inorganic contaminants. U.S. Pat. No. 6,410,256 to Ceri et al. discloses a method of making biofilms. U.S. Pat. No. 6,051,423 to Ceri et al. discloses bacteria are incubated to form a biofilm on projections by providing a flow of liquid growth medium across projections and an assay made of the resulting biofilm. U.S. Pat. No. 5,624,815 to Grant et al., U.S. Pat. No. 5,792,430 to Hamper and U.S. Pat. No. 4,753,775 to Ebersole et al. disclose the biological material in which the liquid sample is drawn over a solid support. McCoy et al. described the Robbins device in the Canadian Journal of Microbiology (1981), volume 27, p. 910 to 917. Ceri et al. described the Calgary biofilm device in the Journal of Clinical Microbiology (1999), volume 37, p. 1771 to 1776.

However, these systems are complicated, costly and time consuming to operate. More particularly, these devices and methods can't to make different thickness of biofilm rapidly.

SUMMARY OF INVENTION

This invention relates to a method and device for making different thickness of biofilms and for determining the effect of various biofilms on the adhesion and corrosion of different materials.

Its purpose is to provide a quick and easy way to create different thickness of biofilms and to evaluate the ability of various biocides of different concentrations to penetrate biofilm. This method is economical as well as occupies minimum amount of space.

Concurrently, the present invention also provides a means to set up an efficient and effective method to evaluate biocide effectiveness against biofilms based on our device.

DETAILED DESCRIPTION

Figure 1:
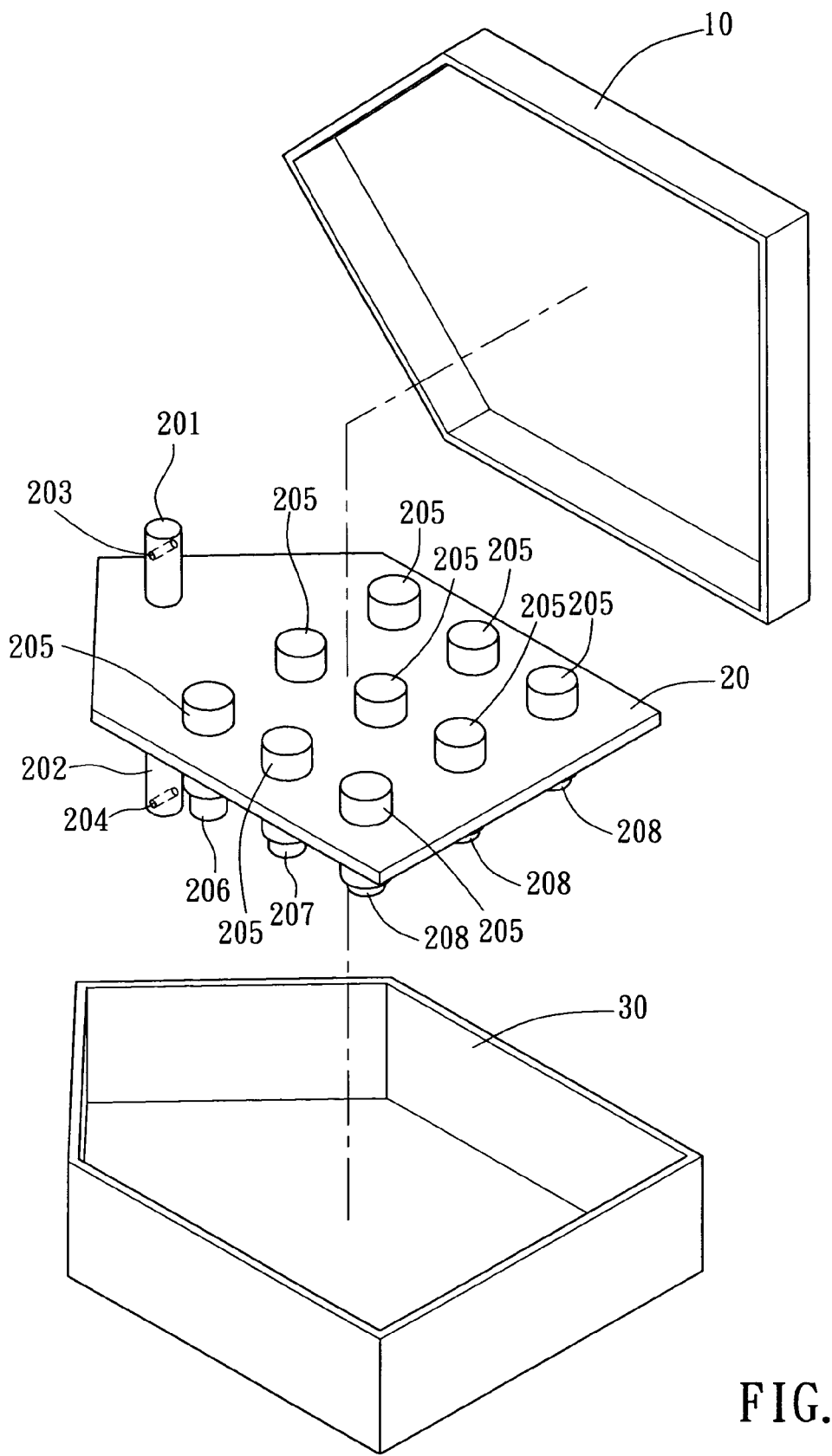
FIG. 1 is an internal view of the biofilm thickness modular device of the present invention.
Figure 2:
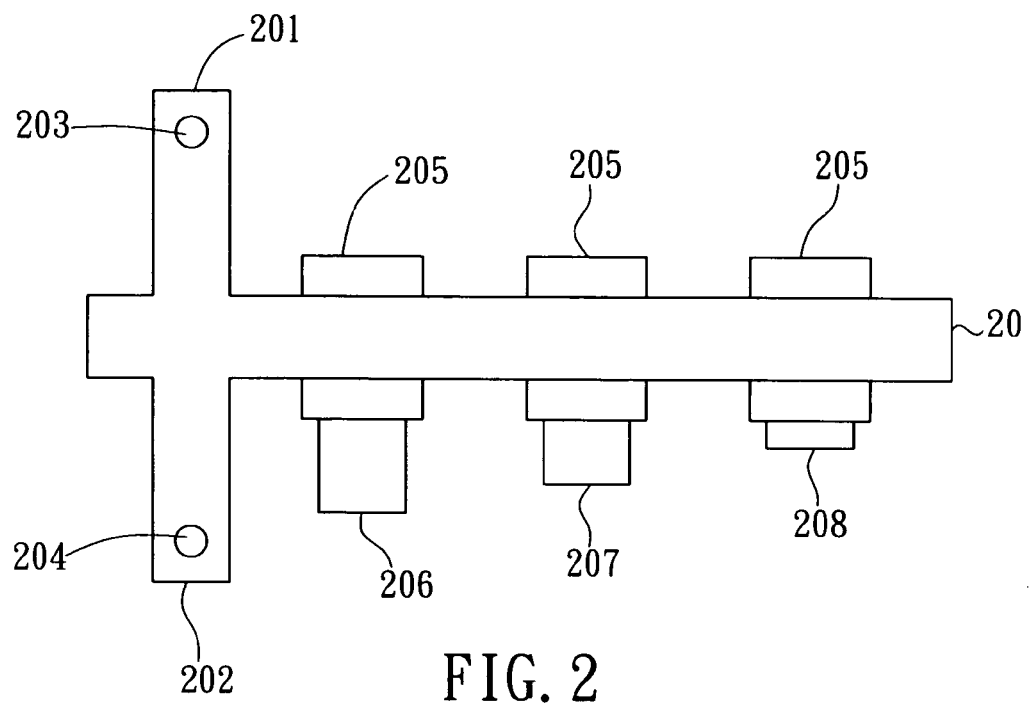
FIG. 2 is a side view of the different heights of biofilm thickness module.
Figure 3:
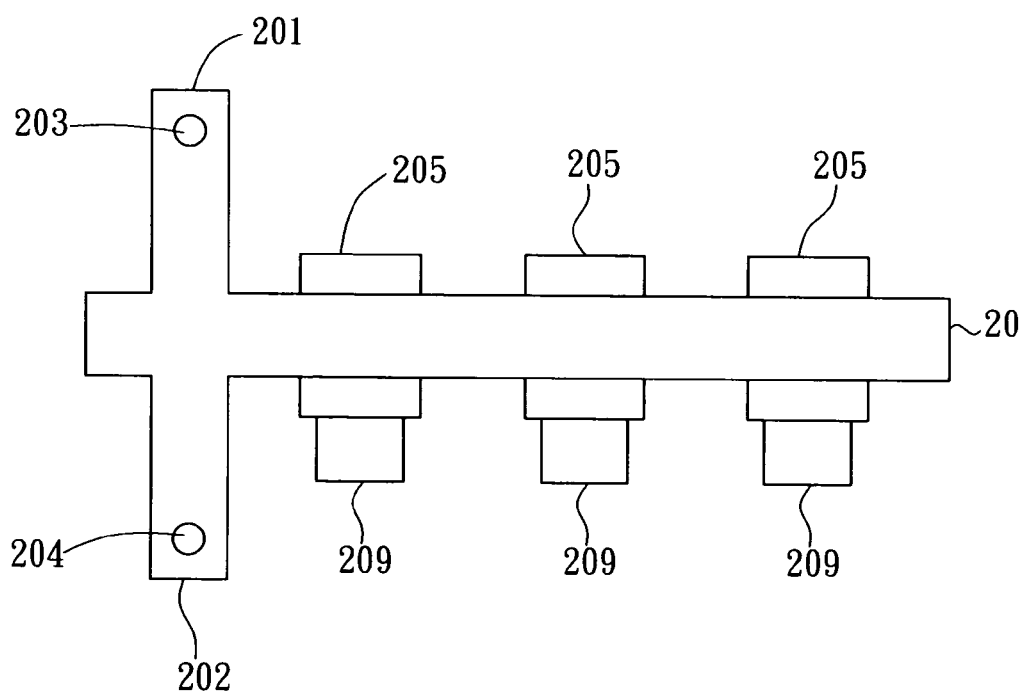
FIG. 3 is a side view of the same height of biofilm thickness module.
Figure 4:
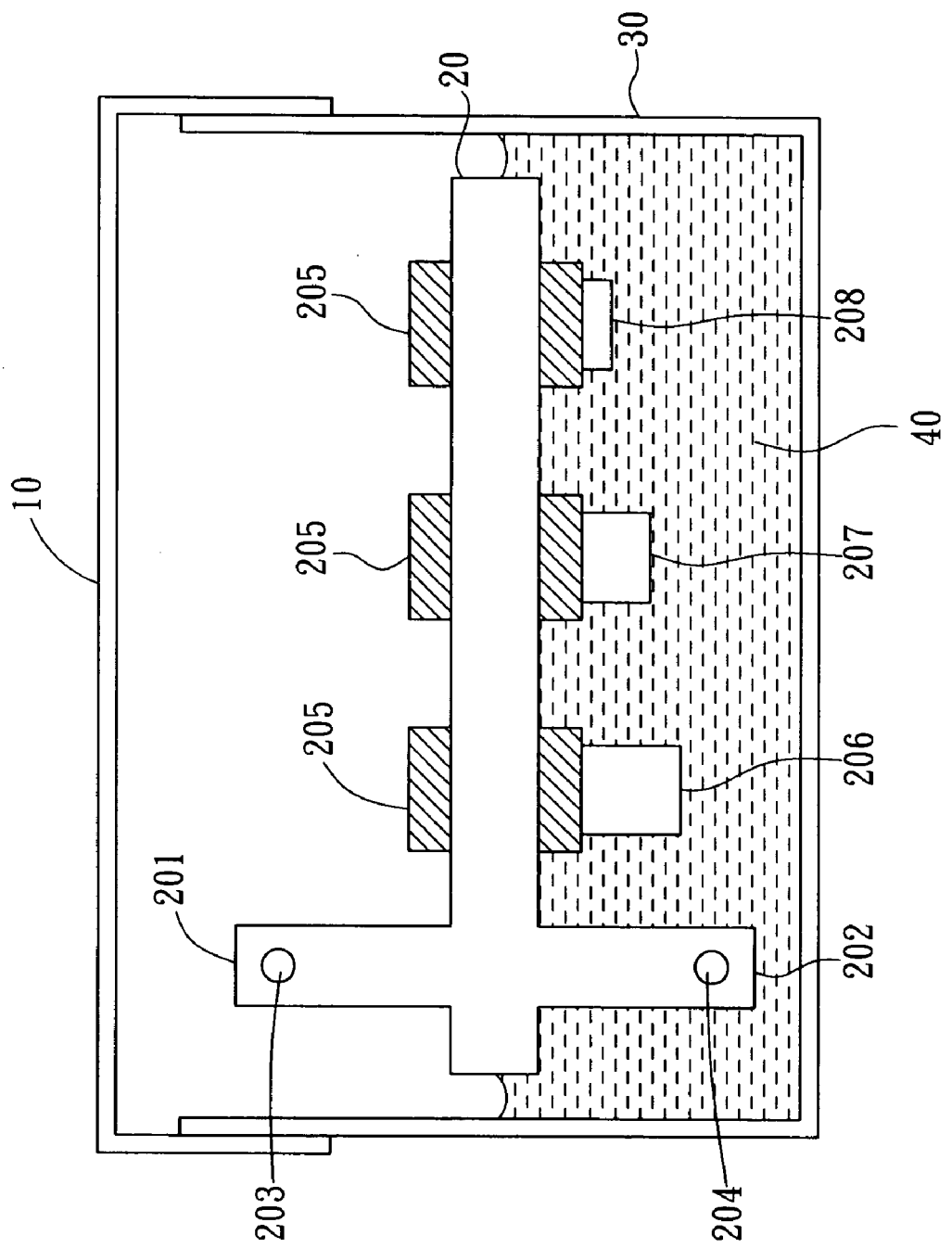
FIG. 4 is a side view of a thickness module for making different thickness of biofilm.
Figure 5:
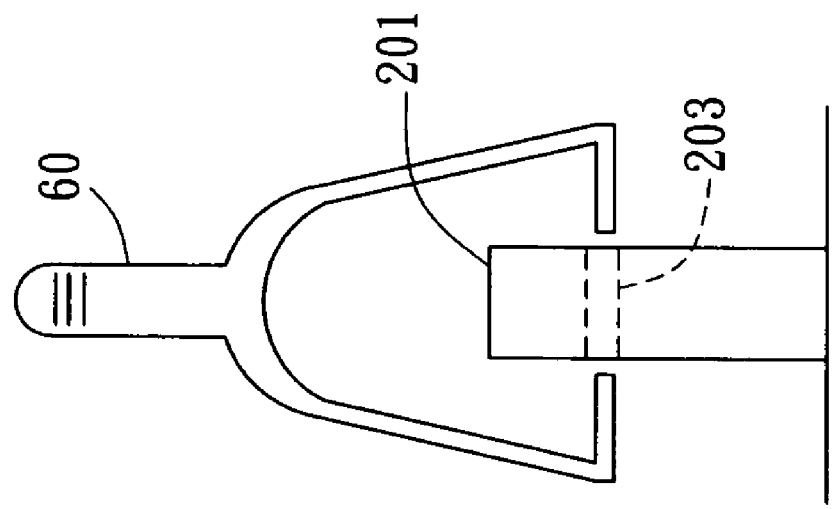
FIG. 5 is a side view of a clamp for pulling up the thickness module.
Figure 6:
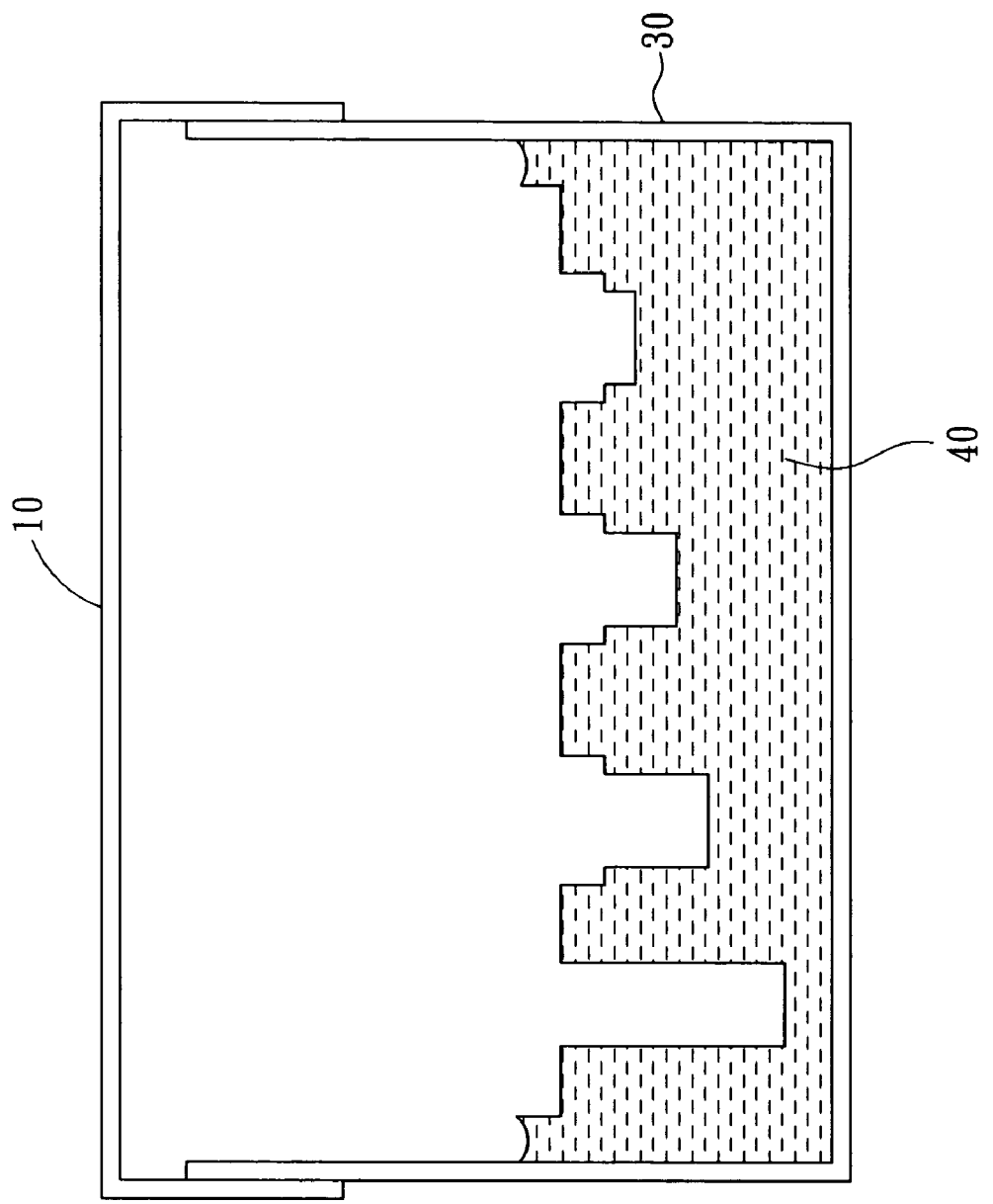
FIG. 6 is a side view of different thickness of biofilm
Figure 7:
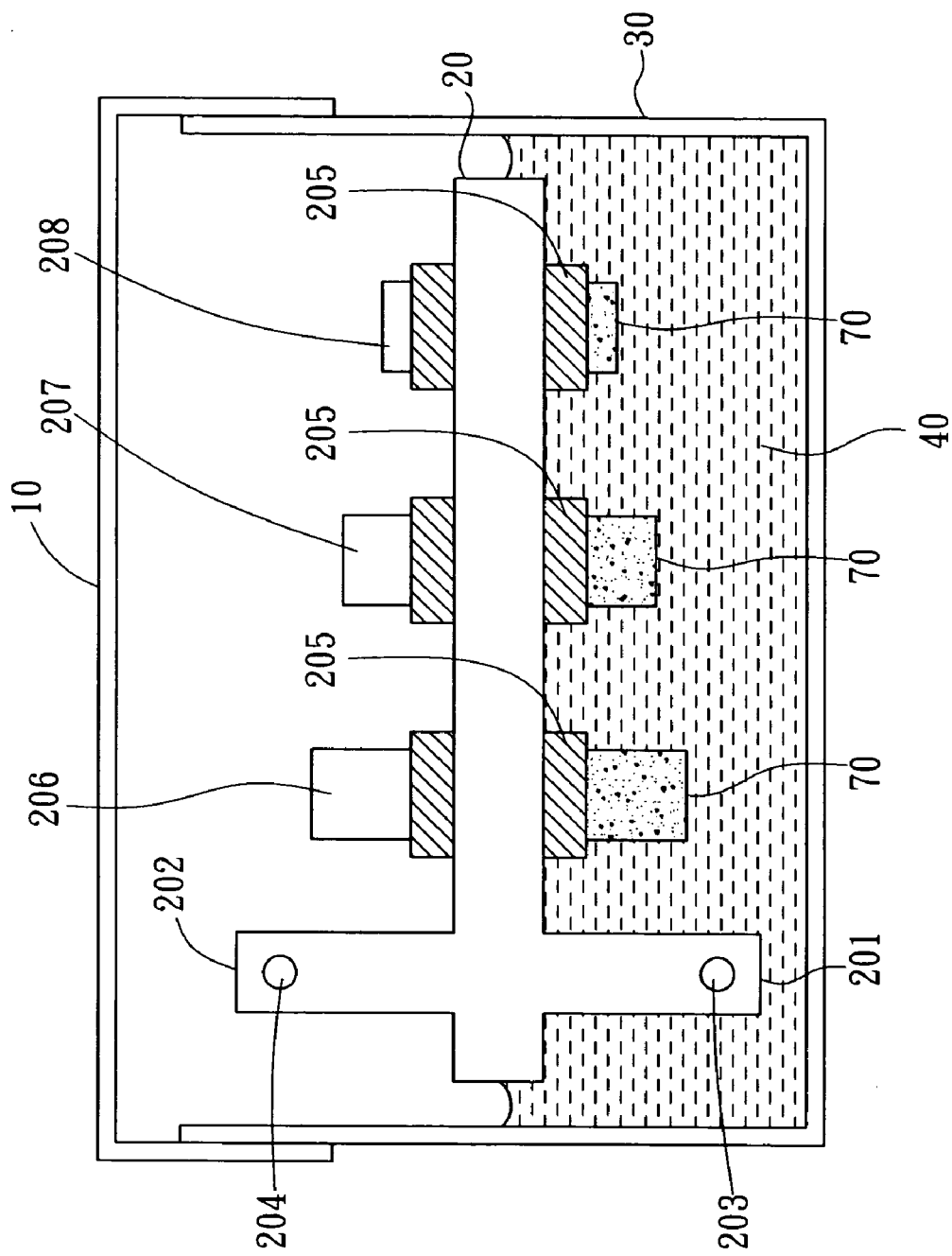
FIG. 7 is a side view of the back of thickness module as a cover.

Please review FIG. 1. It consists of an interior perspective view of our device. The present invention consists of a pentagonal dish cover (10), a thickness module (20) and a pentagonal dish bottom (30). On the underside of the thickness module (20) are a number of protrusions of different heights (206), (207), (208) (see FIG. 2) or of the same height (209) (see FIG. 3). The heights of these protrusions correspond to the thickness of the biofilm that we wish to create. The best practical cross-section of these protrusions is round. After one pours agar (40) into the dish bottom (30), puts the thickness module (20) onto the surface of the agar, the thickness module will buoy on the agar and waits for it to set (see FIG. 4), then one can pull up the thickness module by a clamp (see FIG. 5) and get some different depth of wells that have been cast onto the smooth surface of the agar (see FIG. 6). After then, one puts the back of the thickness module as a cover (205) to cover onto the wells that contains the tested microbes (70), and places the dish cover (10) onto the dish bottom (30) which now contains agar with a smooth surface and a number of desired biofilm depths (see FIG. 7). The cover can keep the thickness of biofilm is constant. Due to the growth rate of microbes is different, and the surface of biofilm is also different (smooth or irregular surface). It is necessary to use a cover to cover the surface of the biofilm to avoid the interaction as above described.

Figure 8:
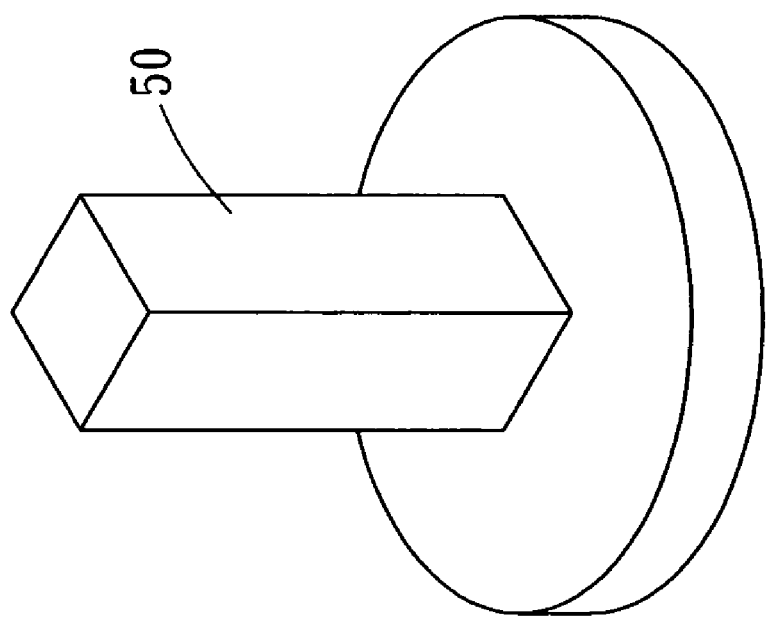
FIG. 8 is an external view of the small cover.
Figure 9:
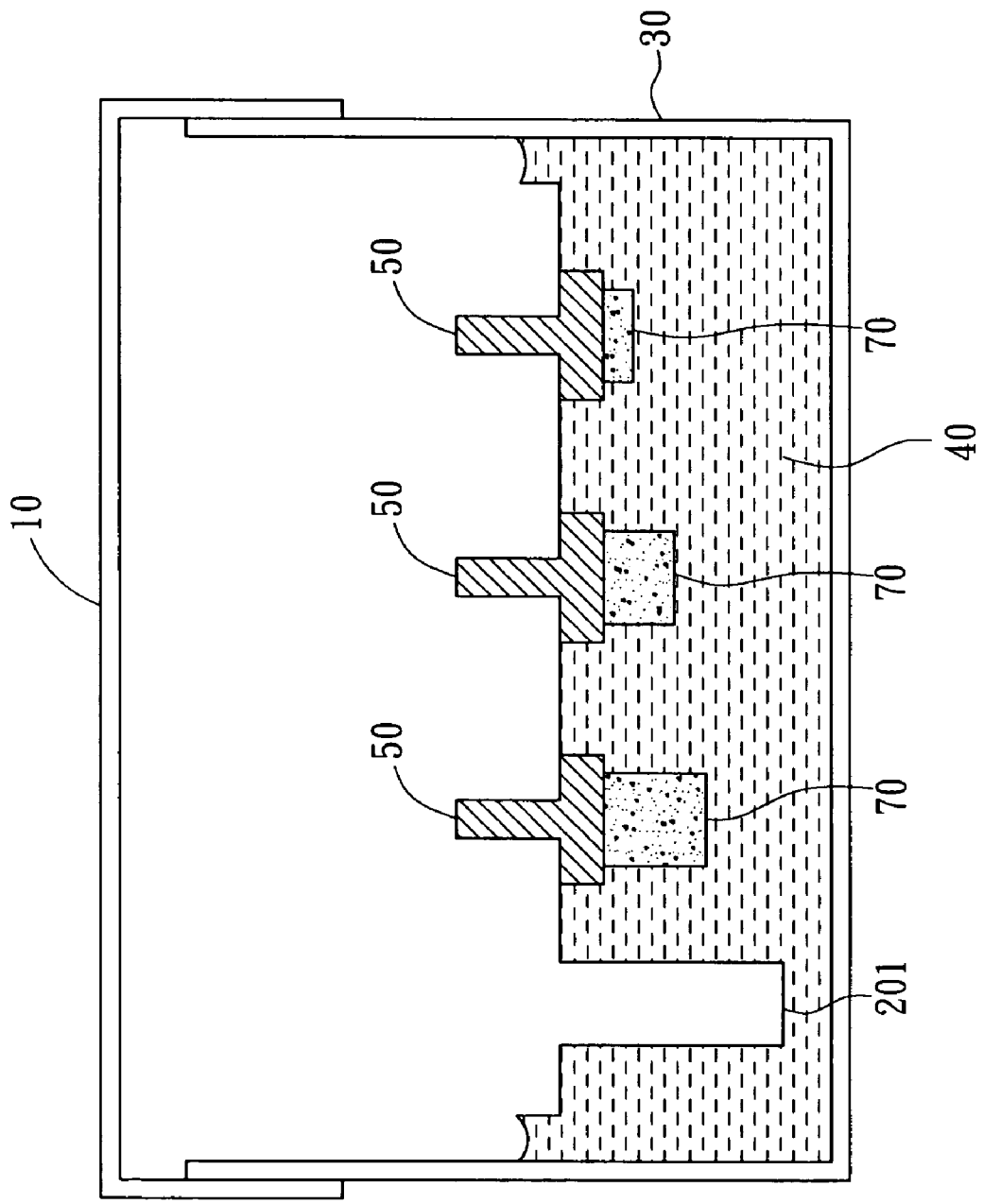
FIG. 9 is a side view of the small cover for covering the biofilm.

Besides, one can make a small cover (see FIG. 8) that is made of different materials, such as plastic, rubber, glass, metal, alloy or implantable medical materials and so on, to test the effect of biofilms on the adhesion and corrosion of these materials base on our device (see FIG. 9).

The evaluation procedure for the effectiveness of biocides or antibiotics against biofilm consists of the following steps:

(a) First, one takes a solution of cultured germ and runs it through a centrifuge, then pours out the suspension to obtain the slime below, which should be of a density of 10.sup.8 to one milliliter above. Take appropriate amount of the slime and fill in the modular holes that we have created in the agar surface mentioned above. Agar will allow germ to carry on its metabolic processes and develop biofilm of different thickness after some time.

(b) Prepare biocides or antibiotics of a given concentration. Pour a fixed amount of it in the dish containing the biofilm of different thicknesses as prepared according to (a) above. Allow it to act on the biofilm for a fixed amount of time under constant temperature in a static state.

(c) Pour out the biocide in the dish and perform an analysis of remaining activity with it. Compare the result with unused portion of the same biocides or antibiotics solution.

(d) Use sterile water to gently rinse the inside of the dish before testing the different thickness biofilms for microbiological activity. This way we can ascertain the effectiveness of a given concentration of biocide in penetrating different thickness of biofilm of a given microbiological entity.

Another experiment could be conducted in which different microbiological entities of the same biofilm thickness have been prepared in the same dish. With a similar procedure as described in (a), (b), (c) and (d) above, we can very quickly evaluate the effectiveness of a given concentration of biocide on penetrating different kinds of microbes.

The present invention also offers a simple way for testing the effect of various biofilms on the adhesion and corrosion of different materials. To prepare the different microbiological entities of the same biofilm thickness, and then puts the small cover which is made of different materials that you want to test onto the surface of biofilm.

Allow the biofilm to act on the touched surface of materials under tested conditions, and then analysis the surface of materials after some time.

One can understand from above that our invention has the advantages of being easy and fast to operate, simple to set up in terms of equipment, making it a practice solution to make different thickness of biofilm and the biocide evaluation problem and a valuable invention for commercial use.

What is claimed is:

1. A thickness module device used in making different thickness of biofilms comprising:

dish including a dish bottom and a dish cover;

an internal thickness module having a number of protrusions of different heights or of the same height on its underside for producing the thickness of biofilms and having a number of protrusions of the same height on it's top surface.

2. A thickness module device as defined in claim 1 wherein the thickness module device is made of plastic, glass or metal.

3. A thickness module device as defined in claim 1 wherein the different thickness of biofilms is between 0.05 mm to 20 mm.

4. A thickness module device as defined in claim 3 wherein the biofilms are selected from at least on of bacteria, actinomyces, fungi or mixture of microbes.

\* \* \* \* \*